United States Patent [19]

Pickford

[11] Patent Number: 5,140,017
[45] Date of Patent: Aug. 18, 1992

[54] COMBATING OF UNDESIRED ORGANISMS

[75] Inventor: Robert J. J. Pickford, North Humberside, England

[73] Assignees: Aquaspersions Limited, Westyorkshire; Humber Growers Marketing Organisation Limited, North Humberside, both of England

[21] Appl. No.: 634,189

[22] PCT Filed: Jul. 12, 1989

[86] PCT No.: PCT/GB89/00790
  § 371 Date: Jan. 14, 1991
  § 102(e) Date: Jan. 14, 1991

[87] PCT Pub. No.: WO90/00351
  PCT Pub. Date: Jan. 25, 1990

[30] Foreign Application Priority Data

Jul. 12, 1988 [GB] United Kingdom ............... 8816542
May 22, 1989 [GB] United Kingdom ............... 8911744

[51] Int. Cl.$^5$ ............ B01J 13/02; C12N 11/10; A61K 9/34; A01N 25/34
[52] U.S. Cl. .................. 514/60; 514/58; 514/54; 514/23; 514/57; 514/778; 514/770; 514/596; 424/405; 424/407; 424/410; 424/404
[58] Field of Search ............. 536/18.3; 424/410, 80, 424/486, 493, 405, 407, 404; 71/65; 514/58, 60, 54, 23, 778, 770, 596

[56] References Cited

U.S. PATENT DOCUMENTS

| | | | |
|---|---|---|---|
| 3,891,756 | 6/1975 | Kasugai et al. | 514/54 |
| 3,920,442 | 11/1975 | Albert et al. | 514/596 |
| 4,034,084 | 7/1977 | Siragusa | 424/180 |
| 4,093,440 | 6/1978 | Denninger et al. | 514/770 |
| 4,182,620 | 1/1980 | Denninger et al. | 514/778 |
| 4,226,855 | 10/1980 | Shigematsu et al. | 424/177 |
| 4,344,857 | 8/1982 | Shasha et al. | 424/486 |
| 4,382,813 | 5/1983 | Shasha | 424/493 |
| 4,582,901 | 4/1986 | Prestwich | 536/83 |
| 4,871,541 | 10/1989 | Shibanai | 514/58 |
| 4,888,325 | 12/1989 | Schroeder et al. | 536/18.3 |
| 4,983,390 | 1/1991 | Levy | 424/410 |
| 4,983,583 | 1/1991 | Ridoux | 514/54 |
| 4,992,275 | 2/1991 | Lush | 424/405 |
| 5,061,697 | 10/1991 | Shasha et al. | 424/405 |

FOREIGN PATENT DOCUMENTS

| | | |
|---|---|---|
| 0230598 | 8/1987 | European Pat. Off. |
| 0179324 | 5/1988 | European Pat. Off. |
| 1574883 | 7/1969 | France |
| 2022568A | 5/1979 | United Kingdom |

Primary Examiner—Ronald W. Griffin
Assistant Examiner—Louise Leary
Attorney, Agent, or Firm—Nixon & Vanderhye

[57] ABSTRACT

Undesired organisms, including insects, mites and fungi, may be combated by application of a composition which comprises a carbohydrate, protein or glycoprotein, or a functionalized derivative of any of these, as an active ingredient. Examples of materials which have been found to have relevant activity are sucrose, hydroxypropyl methylcellulose, starch and dextrinised starch. Examples of undesired organisms which have been found to be affected are whiteflies, thrips, red spider mites, cucumber powdery mildew and oat powdery mildew.

12 Claims, No Drawings

COMBATING OF UNDESIRED ORGANISMS

This invention relates to the combating of undesired organisms and is concerned particularly, although not exclusively, with the combating of insects, mines and fungi.

Chemical methods of controlling undesired organisms are well known. However, organisms have an ability to evolve, so that after a period of time their resistance to a particular chemical tends to increase. Accordingly, new pesticides must continually be developed so that man is always at least one step ahead of the—pests—always having a pesticide to which the target pest has not yet become resistant.

Another consideration when developing a pesticide, besides the toxicity to the target organism, is whether the pesticide will have detrimental effects on desirable organisms. Thus, before a new pesticide can be marketed, stringent tests must be carried out to ascertain its safety in the eco-system and the environment as a whole.

We aim to improve upon this situation by providing a pesticide which may be advantageous in at least some of the aforementioned respects.

According to a first aspect of the present invention, there is provided a method of combating an undesired insect, mite or fungal organism, comprising the step of applying a composition to an area in which it is desired to combat the organism, characterised in that the composition comprises, as active ingredient, a carbohydrate selected from starch and/or a derivative thereof selected from an oxidized starch, a dextrinised starch, a starch ether, a cationic starch, a phosphate starch, a starch acetate; or an analogous derivative of amylose or amylopectin.

A composition for use in the method of the invention may include a wetting agent and/or a preservative and/or biocidal agent and/or an inert chemical buffer.

A preferred carbohydrate for use in the method of the present invention is a dextrinised starch, commonly called a starch-dextrin, or simply a dextrin. A "dextrin" is commonly defined as a intermediate product or products in the transformation of starch into maltose or D-glucose.

Dextrinisation may take place by one of various methods, including enzymic reaction, in particular by amylases on starch; by the action of *Bacillus Macerans*, to yield cyclic dextrins having six and seven D-glucose units; by acid hydrolysis in aqueous media; and by the action of heat with or without acid being present, on starch. The latter dextrins, sometimes called pyrodextrins, are especially preferred carbohydrates for use in the method of the invention.

Pyrodextrins are commonly made by spraying dried starch with an acid, typically a mineral acid, usually hydrochloric acid but sometimes nitric acid, then drying the sprayed starch to leave a 1-5% water content. The acidified starch is hydrolysed and reverted by heating. At a final temperature of 95°-120° C., a white pyrodextrin is produced, typically having a low ratio of branched derivatives. At a final temperature of 150°-180° C., a canary-yellow dextrin is produced, having a higher degree of branching, approximately 20%, and being less viscous, than the white dextrins. Without acid but with a longer reaction time and a final temperature of 170°-195° C., the product is a British gum dextrin. Following the final heating step, cooling is rapid to prevent overconversion. The acid may be neutralised at this point in the process if required.

In the present invention, the use of canary-yellow dextrins is particularly preferred.

When starch or a starch derivative is used in the present invention, starch or a starch derivative of any origin may be employed, for example a starch or starch derivative derived from tubers, such as potato, or derived from cereals, such as corn or rice. Very interesting activity has been observed with pyrodextrins derived from such potato starch.

An active ingredient may be synthetic or natural, although natural active ingredients are likely to be used, for economic reasons.

The area to which the composition is applied may be already infected with a target organism or subject to or at risk of such infection, the treatment of the area then being prophylactic. The dosage of active ingredient used may, for example, be from about 3 to about 1150 kg/ha, suitably about 50-150 kg/ha. A carrier in a composition used in a method according to the invention is any material with which the active ingredient is formulated to facilitate application to the area to be treated, which may for example be a plant, seed or soil, or to facilitate storage, transport or handling. A carrier may be a solid or a liquid, including a material which is normally gaseous but which has been compressed to form a liquid, and any of the carriers normally used in formulating biocidal compositions may be used.

Agricultural compositions are often formulated and transported in a concentrated form which is subsequently diluted by the user before application. The presence of small amounts of a carrier which is a surface-active agent facilitates this process of dilution. Thus, preferably at least one carrier in a composition used in the method of the invention is a surface-active agent. For example the composition may contain at least two carriers, at least one of which is a surface-active agent.

Compositions might for example be formulated as wettable powders, dusts, granules, solutions, emulsifiable concentrates, emulsions, suspension concentrates and aerosols.

The composition may be suitably applied in solution. It is be preferred that a surface active agent is provided to facilitate wetting, particularly if the solution is a colloidal solution. Aqueous solutions are preferred.

A surface active agent may be an emulsifying agent, a dispersing agent or a wetting agent; it may be nonionic or ionic. Examples of suitable surface active agents include the sodium or calcium salts or polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenyl or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; polymers of ethylene oxide and copolymers of ethylene oxide and propylene oxide; and alkali metal salts of fatty acids containing at least 10 carbon atoms.

Preferred wetting agents are the alkali metal salts of fatty acids containing at least 10 carbon atoms, for example sodium laurate, and condensation products of alkyl phenols with ethylene oxide and/or propylene oxide, for example nonyl phenyl ethylene oxide condensate.

The combination of an active ingredient and a wetting agent is thought to be particularly important in obtaining an effective liquid composition.

Suitably, a liquid composition comprises about 0.05-5 wt %, preferably about 0.1-3 wt %, of wetting agent(s).

The presence of a preservative to prevent degradation or spoiling of an active ingredient as described above is thought to be important. Small amounts of a preservative, for example about 0.001 to 1 wt %, in particular about 0.01 to 0.5 wt %, based on the liquid composition to be applied to the area, may be suitable.

A preferred liquid composition to be applied comprises about 0.01 to 50 wt % active ingredient (as defined above); about 0.05 to 5 wt % wetting agent, and about 0.001 to 1 wt % preservative.

A particularly preferred liquid composition to be applied comprises about 0.1 to 10 wt % active ingredient (as defined above); about 0.1 to 3 wt % wetting agent, and about 0.1 to 1 wt % preservative.

Suitably, the composition may contain at least about 0.01% by weight of the carbohydrate, suitably about 0.1 to 50%. Preferably, the composition contains about 0.1 to 10% by weight of the carbohydrate.

Most preferably, the composition contains about 0.1 to 5% by weight of the carbohydrate. Especially preferred is a composition containing about 0.1 to 3% by weight of the active ingredient, especially about 0.1 to 2%.

The composition may preferably contain an active ingredient as described above, in the range x to y, where:

x may have any value between 0.1 and 49.9 in increments of 0.1;

y may have any value between 0.2 and 50 in increments of 0.1; and the value of x is always less than the value of y.

The composition may include a salt, so provided in order to affect the osmotic pressure or diffusion gradient between the organism and its surroundings.

In living systems, it is often found that the pH of solutions is important. Accordingly, it may be desirable to buffer the composition in order to maintain it at a generally constant pH.

The target organisms may be insects. The composition may be applied to insect eggs. Alternatively, the composition may be applied whilst the insects are in the form of larval instars, pupal instars, or adult insects. The insects may, for example, be aphids, such as greenfly; whitefly, including glasshouse whitefly (*Trialeurodes vaporariorum*) and tobacco whitefly (*Bemisia tabacci*); or thrips.

Although the mode of action of the composition on insects is not known, it is thought that it may act to contain them in, for example, their eggs, larval instar form, pupae form, or restrain them in their adult form, having a mechanical effect such that the insects are physically hindered from developing and/or moving; and/or may act on the respiratory tract of the insects, perhaps by asphyxiation; and/or act by dehydration. However, it should be stressed that the action is clearly not that of a simple insect trap, such as a flypaper.

It should also be stressed that the composition used in the invention is not used with a conventional synthetic chemical pesticide to form an insect bait, as has been proposed, using starch, in WO 85/04074; nor as a casing for a conventional synthetic chemical pesticide, to aid shelf life of the pesticide, as has been proposed for starch. Rather than a carrier or adjunct, the carbohydrate is used in the method of the present invention as an active pesticidal agent.

The organisms may be mites (acarina), for example red spider or clover mites in the form of adults or otherwise. Again, the mode of action is not known, although the mechanisms described above for insects may operate.

The organisms may be fungi, for example rusts or mildews, especially powdery mildews, including mildews of cereals. Again the mode of action is not known, although it may be a matter of mechanical containment, for example to prevent spores from bursting, or the provision of a barrier layer which prevents spores which land on a leaf from accessing the nutrients within the leaf, or which prevents spores from recognising the leaf as an acceptable host.

In general, therefore, it may be desirable in the method of the invention that a composition for use therein is a somewhat sticky solution, either immediately upon application or after at least some curing/drying of the solution. However, it must again be emphasised that, whatever the mode of action, it is more subtle than to simply provide an insect trap of conventional type, in situ.

It is thought that if, indeed, the mode of action is not via a biochemical pathway but by a physical action, as suggested above, that the development of resistance by target organisms is unlikely to occur.

Since it is the chemical action of conventional pesticides which generate the selective pressure that gives rise to pest resistance, then it is probable that a change in the physical environment is far less likely to cause pest resistance. The enzymic mechanisms which enable pest resistance are not likely to overcome the new environmental conditions created by starch-dextrin or other active materials as described herein.

The use of a naturally occurring material as an active pesticidal ingredient has obvious environmental attractions.

It should be appreciated that starch or starch derivatives noted herein, are generally non-toxic. Accordingly, it may be advantageous to use the compositions on edibles, for example, tomatoes, to combat tomato leaf minor, or in other cases where the use of potentially toxic pesticides may have detrimental and/or undesirable effects.

Since active ingredients as described herein are used in the food industry then there is little toxicological risk to the consumer of any food crop sprayed in this way. Similarly, as most such materials leave no toxic residue, there is little chance of any detrimental effect to the wider environment, and its use is likely to be compatible with current biological control methods.

The area to which the composition is applied may comprise part of a plant. Alternatively, the composition may be applied to an area adjacent to a plant, for example the soil or ground. It may comprise the ground, for example the floor of a greenhouse, when it is desired to control species, such as thrips, which may pupate on the floor rather than on the leaves of plants. The method of the invention may be applied in an agricultural environment, or a horticultural environment, for example a glasshouse. The method is of particular interest to control pests in glasshouses, where the problems can be particularly severe, and the deleterious effects of conventional synthetic chemical pesticides especially pronounced.

The composition of the invention may include a foliar feed, and such a composition is particularly useful in a horticultural environment, especially a glasshouse.

Suitably, the active material as described above is substantially the sole active ingredient in the composition. Preferably, at least, it is a major active ingredient in the composition. In particular, it is preferred that the composition does not contain a "conventional" synthetic chemical pesticidal agent.

Another aspect of the invention relates to a method of combating an undesired insect or mite organism, comprising the step of applying a composition to an area in which it is desired to combat the organism, characterised in that the composition comprises, as active ingredient, a carbohydrate selected from a cellulose or a cellulose ether.

The invention will now be further described, by way of example, with reference to the following:

EXAMPLE 1

Preparation of Biocidal Composition

A biocidal composition in accordance with the invention was prepared by mixing the following constituents:
AVEDEX 58 MD 14C (Trade Mark) canary-yellow dextrin, derived from potato starch by acid pyrolysis (starch-pyrodextrin) - 1.5%
0.2 wt % PBI SPREADER (Trade Mark) wetting agent (a nonyl phenol ethylene oxide condensate)
0.015 wt % sodium benzoate (preservative)
water to 100%

EXAMPLE 2

Activity against Red Spider Mites (*Tetranychus urticae*)

Plants of *Cucimus sativus* c.v. Cillia were grown in 45 litre pots in a greenhouse temperature set at 21° C.–26° C. to the first true leaf stage. Ten red spider mites (*Tetranychus urticae*) were introduced onto the first true leaf. Plants were sprayed using a domestic sprayer with the composition of Example 1 until the solution started to run off the leaf.

In a separate treatment, infected plants were sprayed with a 0.2 wt % solution of the wetting agent. In a third treatment an aqueous formulation was made up of 0.5 g/l of TORQUE (Trade Mark), a commercial formulation of fenbutatin oxide acaricide. In accordance with tho manufacturer's instructions no wetting agent or preservative was added.

Replication was twenty fold and the pots were arranged in randomised blocks. The numbers of red spider mites were determined after 18 days.

The following Table 1 shows that the starch-dextrin solution was more effective than the commercial acaricide in killing red spider mites. It was possible to tentatively conclude that death was caused by physical means, for example, by asphyxiation, dehydration or by trapping or any combination of these processes.

TABLE 1

|  | Wetting Agent solution | Starch-dextrin solution | Fenbutatin oxide solution |
|---|---|---|---|
| Mean | 174.8 | 19.1 | 38.0 |
| Std error | 19.5 | 3.3 | 12.0 |

EXAMPLE 3

Activity against Cucumber Powdery Mildew (*Sphaeiotheca fuliginea*)

Plants of *Cucumis sativus* c.v. Cillia, grown as described in Example 2, were inoculated with cucumber powdery mildew (*Sphaeiotheca fuliginea*) sixty minutes after the plants had been sprayed with the starch-dextrin solution of Example 1, the wetting agent solution described in Example 2, and a 0.025% solution of RUBIGAN (Trade Mark), a commercial fungicide, namely a fenamirol formulation. In accordance with the manufacturers instructions no wetting agent or preservative was added. The number of pustules was assessed after 10 days. Replication was twenty fold and the pots were arranged in randomised blocks.

Table 2 below shows that starch-dextrin was effective in reducing pustule formation by 57%, and spore germination was reduced on the leaves sprayed with starch-dextrin solution.

TABLE 2

|  | Wetting Agent solution | Starch-dextrin solution |
|---|---|---|
| Mean | 164.1 | 69.6 |
| Std error | 4.0 | 3.3 |

The fenarimol gave substantially 100% control.

Again, it may be tentatively concluded that control by the starch-dextrin solution was caused by a physical action.

EXAMPLE 4

Example 3

Activity against Western Flower Thrips (*Frankliniella occidentalis*)

A substantial population of thrips was introduced to a large number of plants of *Cucumis sativus* c.v. Corona, on Day 1. The plants were sprayed to run off with the composition of Example 1, as described above, on Days 2 and 14. Thrip populations was assessed on Days 1, 3, 6, 9, 15 and 22, by sampling 70 leaves on each occasion. Total thrip population levels were as follows:
Day 1—74
Day 3—11
Day 6—35
Day 9—19
Day 15—6
Day 22—18

EXAMPLE 5

Activity against Whitefly (*Trialeurodes vaporariorum*)

(a) Tests against scales (pupae)

Tobacco leaves heavily infested with whitefly scales were used for this test. Tobacco leaves were cut into squares, each infected with approximately 1000 scales. The following aqueous compositions were sprayed onto the leaves to run off:

|  |  | Result |
|---|---|---|
| Composition No. 1: | 0.2% wt PBI SPREADER | 0% death |
| Composition No. 2: | 2.5% wt AVEDEX | 8.3% death |
| Composition No. 3: | 2.5% wt AVEDEX + 0.2% wt PBI SPREADER | 29.9% death |
| Composition No. 4: | 5% wt AVEDEX | 26.9% death |
| Composition No. 5: | 5% wt AVEDEX + 0.2% wt PBI SPREADER | 18.5% death |

(b) Tests against eggs

Tobacco leaves heavily infested with whitefly eggs were used for this test. Tobacco leaves were cut into squares, each infected with approximately 600 eggs. Compositions Nos. 1 to 5 as described above were sprayed onto the leaves to run off, with the following results:

|  | Result |
|---|---|
| Composition No. 1: | 0% death |
| Composition No. 2: | 85.8% death |
| Composition No. 3: | 94.7% death |
| Composition No. 4: | 95.5% death |
| Composition No. 5: | 98.4% death |

EXAMPLE 6

Activity against Greenfly (*Aphids gossypii*)

A simple test was carried out whereby an aqueous composition containing 0.5% wt AVEDEX and 0.1% wt PBI SPREADER was sprayed onto leaves of cucumber plants infested with greenfly. Visual inspection the following day indicated 100% death of the greenfly.

EXAMPLE 7

Activity against Whitefly Partially Controlled by Parasitic Wasps (Encarsia)

It is believed that yellowing of plants is produced as a consequence of the presence of a pseudo beet-yellows virus which is known to be transmitted by whitefly.

In an attempt to alleviate this problem, a biological control may be used, which control is aimed at killing the transmitters of disease, namely the whitefly. To this end, a defined amount of female parasite wasps are introduced into the greenhouse, which parasites parasitize larvae of the whitefly, eventually causing death to the whitefly. The new parasites are contained within whitefly pupae, in order to parasitize them. However, this method is not wholly effective and it would be desirable to use an additional form of control, which assisted the parasites in combating the whitefly whilst having no or a lesser detrimental effect on the parasites.

Experiments have shown that, employing treatments as described above, a substantial amount of new whitefly adults are contained, dead, in their respective pupae, unable to escape therefrom. In fact, in experiments, it has been noted that some of the adults show no signs of having broken through the cuticle of their pupae. Others are found to have partially broken through the cuticle but are unable to fully emerge from the pupae. It is thought that the starch-dextrin may mechanically inhibit the escape of the adult, which eventually dies from exhaustion, due to lack of essential nutrients which are not available within the pupae.

However, it has also been noted that the parasites are able to escape from the pupae in substantial number, apparently able to overcome any inhibition by the starch-dextrin. Whilst some adult parasites are killed, the overall effect of the composition was clearly in favour of the parasite.

OTHER ACTIVITY

Activity has also been found against oat mildew.

Generally, tests against fungi have shown that a starch-dextrin solution has fungicidal effect when sprayed onto spores, or on to plant surfaces, such as leaves, later contacted by spores. In the former case, it that the mode of action is to inhibit bursting of spores, whilst in the latter, it may be that the starch-dextrin provides a barrier to a spore which has alighted on a leaf, thereby inhibiting its hyphae from "plugging into" the food channels of the leaf of the plant, the spore accordingly being unable to acquire any nutrients to provide energy for its germination, from the plant. It may also inhibit spore release and dispersal.

OTHER ACTIVE COMPOSITIONS

Activity has been shown by a simple aqueous solution of household starch intended for use in stiffening collars and cuffs of shirts.

A composition comprising 5% wt sucrose, 0.2% wt PBI SPREADER, and water to 100%, showed a high kill rate against red spider mites and greenfly, when sprayed to run off onto bean leaves (infested with the red spider mites) and tobacco leaves (infested with the greenfly).

A composition encomprising 5% wt METHOCEL J12MS (Trade Mark), hydroxypropyl methylcellulose, ex. Dow Chemicals, 0.2% wt PBI SPREADER and water to 100%, showed a high kill rate against red spider mites and greenfly, when sprayed to run off onto bean leaves (infested with the red spider mites) and tobacco leaves (infected with the greenfly). It was observed that rapid dehydration and body collapse of the pests occurred.

Starch-dextrin or other materials as defined herein can be expected to have activity against a broad range of insect, mite and fungal pests.

I claim:

1. A method of treatment of a plant to combat an undesired insect, mite or fungal organism which is infecting the plant or may subsequently infect the plant, comprising the step of the foliar application of an effective amount of a composition consisting essentially of, as active ingredient, a carbohydrate selected from the group consisting of starch, amylose, amylopectin, a derivative of said starch, said derivative being selected from the group consisting of an oxidized starch, a dextrinized starch, a starch ether, a cationic starch, a phosphate starch and a starch acetate, and an analogous derivative of amylose or amylopectin.

2. A method as claimed in claim 1, wherein the carbohydrate is selected from starch, a dextrinized starch, and an analogous derivative of amylose or amylopectin.

3. A method as claimed in claim 1, wherein the carbohydrate is selected from a dextrinized starch and an analogous derivative of amylose or amylopectin.

4. A method as claimed in claim 1, wherein the dextrinized material is a pyrodextrin derived from starch, amylose or amylopectin.

5. A method as claimed in claim 1, wherein the dextrinized material is a pyrodextrin derived by spraying starch, amylose or amylopectin with an acid, drying the acidified material to leave a water content of 1-5 wt %, hydrolyzing the acidified and dried material, and subjecting it to a temperature of 150°-180° C.

6. A method as claimed in claim 1, wherein the dextrinized material is derived from tubers or cereals.

7. A method as claimed in claim 1, wherein the dextrinized material is derived from potatoes.

8. A method as claimed in claim 1, wherein the dosage of carbohydrate active ingredient is 50-150 Kg/ha.

9. A method according to claim 1, wherein said composition is in the form of a liquid composition.

10. A method according to claim 9, wherein said composition comprises 0.05 to 5 weight percent of a wetting agent.

11. A method according to claim 9, wherein a foliar feed is present.

12. A method of treatment of a plant to combat an undesired insect, mite or fungal organism which is infecting the plant or may subsequently infect the plant, comprising the step of the foliar application of a composition consisting essentially of, as active ingredient, a carbohydrate selected from the group consisting of cellulose and a cellulose ether.

* * * * *